United States Patent
Jian et al.

(10) Patent No.: US 11,116,706 B2
(45) Date of Patent: Sep. 14, 2021

(54) BLEACHING COMPOSITION COMPRISING PIGMENT AND METHOD FOR BLEACHING OF KERATIN FIBERS

(71) Applicant: KAO GERMANY GMBH, Darmstadt (DE)

(72) Inventors: Niu Jian, Darmstadt (DE); Steven Breakspear, Darmstadt (DE); Bernd Nöcker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 16/954,785

(22) PCT Filed: Dec. 6, 2018

(86) PCT No.: PCT/EP2018/083854
§ 371 (c)(1),
(2) Date: Jun. 17, 2020

(87) PCT Pub. No.: WO2019/121046
PCT Pub. Date: Jun. 27, 2019

(65) Prior Publication Data
US 2021/0085575 A1 Mar. 25, 2021

(30) Foreign Application Priority Data

Dec. 22, 2017 (EP) .................................... 17210249
Feb. 1, 2018 (EP) .................................... 18154728

(51) Int. Cl.
| | | |
|---|---|---|
| *A61Q 5/08* | (2006.01) | |
| *A61K 8/22* | (2006.01) | |
| *A61K 8/04* | (2006.01) | |
| *A61K 8/06* | (2006.01) | |
| *A61K 8/41* | (2006.01) | |

(52) U.S. Cl.
CPC ............... *A61K 8/22* (2013.01); *A61K 8/044* (2013.01); *A61K 8/06* (2013.01); *A61K 8/416* (2013.01); *A61Q 5/08* (2013.01); *A61K 2800/31* (2013.01); *A61K 2800/43* (2013.01); *A61K 2800/48* (2013.01); *A61K 2800/596* (2013.01); *A61K 2800/882* (2013.01)

(58) Field of Classification Search
CPC .... A61K 8/22; A61K 2800/882; A61K 8/416; A61K 2800/31; A61K 8/06; A61K 2800/43; A61K 2800/48; A61K 8/29; A61K 8/044

USPC .......................................................... 424/62
See application file for complete search history.

(56) References Cited

U.S. PATENT DOCUMENTS

| | | |
|---|---|---|
| 6,872,228 B1 | 3/2005 | Lenzi-Brangi |
| 2001/0039685 A1 | 11/2001 | Gutkowski |
| 2002/0179109 A1* | 12/2002 | Lenzi-Brangi ............ A61K 8/41 132/208 |
| 2003/0206877 A1 | 11/2003 | Lenzi-Brang et al. |
| 2006/0248663 A1 | 11/2006 | Tremblay et al. |
| 2011/0240054 A1* | 10/2011 | Pratt ........................ A61K 8/22 132/208 |
| 2012/0024309 A1* | 2/2012 | Pratt ........................ A61K 8/22 132/208 |
| 2012/0031423 A1* | 2/2012 | Wood ........................ A61K 8/64 132/208 |
| 2013/0263878 A1 | 10/2013 | Pratt et al. |
| 2014/0158150 A1* | 6/2014 | Schoepgens ............. A61K 8/22 132/208 |

FOREIGN PATENT DOCUMENTS

| | | | |
|---|---|---|---|
| DE | 29722990 U1 | 5/1999 | |
| EP | 00 70074 A2 | 1/1983 | |
| EP | 1 598 052 A1 | 11/2005 | |
| EP | 1598052 A1 * | 11/2005 | ............... A61Q 5/10 |
| EP | 2686386 A2 | 1/2014 | |
| FR | 2994652 A1 | 2/2014 | |
| JP | 2015-123019 A | 7/2015 | |
| WO | 00/76469 A1 | 12/2000 | |
| WO | 02/078662 A1 | 10/2002 | |

OTHER PUBLICATIONS

International Search Report dated Mar. 12, 2019, in connection with PCT International Application No. PCT/EP2018/083854.
Written Opinion in connection with PCT International Application No. PCT/EP2018/083854.

* cited by examiner

Primary Examiner — Eisa B Elhilo
(74) Attorney, Agent, or Firm — Norris McLaughlin, P.A.

(57) ABSTRACT

The invention is directed to a three-part bleaching composition and method comprising pigments in a third composition. It has unexpectedly been found that an third composition comprising pigments increase the contrast between bleaching composition and keratin fibers to a degree which allows for a more accurate judgement of the desired end point of bleaching during the bleaching process.

15 Claims, No Drawings

BLEACHING COMPOSITION COMPRISING PIGMENT AND METHOD FOR BLEACHING OF KERATIN FIBERS

This application is the U.S. National Stage of International Application No. PCT/EP2018/083854, filed Dec. 6, 2018, which claims foreign priority benefits under 35 U.S.C. § 119 of European Application Nos. 17210249.3, filed Dec. 22, 2017 and 18154728.2, filed Feb. 1, 2018, the disclosures of which are incorporated herein by reference.

The present invention is directed to a three-part bleaching composition comprising pigments, a method for bleaching keratin fibers, preferably human keratin fibers, more preferably human hair, and kit-of-parts.

BACKGROUND OF THE INVENTION

Many customers with dark hair desire a lightening of their hair color to follow current beauty trends and to allow for the application of lighter artificial colors to their hair. Once a customer receives a bleaching service to lighten the hair color, the end point of the bleaching service is determined by judgement of the naked hair dresser's eye. It is not uncommon that upon rinsing and shampooing of the customer's hair a dissatisfactory result of lightening is revealed. The reason for this disappointment is that the hair dresser stopped the bleaching reaction too early because he/she was misled by the low contrast between the white bleaching composition and the progress of hair lightening. In such a case the hair dresser usually decides to reapply the bleaching composition and to continue the bleaching process up to the desired degree of lightening.

However, the double application of bleaching compositions is not only an unnecessary cost of goods, but also unnecessarily extends the customers presence in the hair dresser's salon. Moreover, the customer is disappointment about the poor judgement of the hair dresser and potentially has to accept higher costs for the visit.

In summary, there is a great desire to deliver a bleaching composition and method which overcome the disadvantages of above, prevent unnecessary double bleaching and improve customer satisfaction.

Colored bleaching compositions are known from FR2994652 and US20030206877 which disclose several insoluble pigments in bleaching compositions such as ultramarine blue, titanium dioxide, yellow aluminium lake, green chromium oxide, and red zirconium lakes.

DE29722990 and WO00/76469 disclose three part compositions having the pigments in an alkaline emulsion, but not in a separate third composition.

US20060248663 discloses bleaching and dyeing compositions comprising carbon black as pigment.

In summary, the prior art is silent on the core of the present invention and none of the prior art is able to solve the problem of the present invention in a satisfactory manner.

SUMMARY OF THE INVENTION

The inventors of the present invention have unexpectedly found that pigments in bleaching compositions enhance the contrast between bleaching composition and keratin fibers to an extent which allows for a better judgement by the naked human eye of the hair dresser and/or customer. Moreover, having the pigments separated in a third composition allows the hair dresser to yield a customized contrast between the color of the ready-to-use bleaching mixture and the color of the keratin fibers of the customer. This further allows the hair dresser to separate the bleaching performance from the contrast performance of the ready-to-use mixture.

Therefore, the first object of the present invention is A three-part bleaching composition for keratin fibers, preferably human keratin fibers, more preferably human hair, comprising a) an anhydrous or aqueous first composition comprising one or more alkalizing agent(s), wherein the anhydrous composition further comprises one or more so bleaching compound(s), b) an aqueous second composition comprising hydrogen peroxide, c) a third composition, preferably an aqueous composition, comprising one or more pigment(s) selected from black pigments and/or brown pigments and/or blue pigments and/or green pigments, wherein the ready-to-use composition is obtained by mixing the first, second, and third compositions, wherein the ready-to-use composition has a pH in the range of 8 to 12, and preferably the total concentration of pigments in the third composition is more than 0.6% by weight, more preferably more than 1% by weight, calculated to the total of the third composition.

The second object of the present invention is a method for bleaching keratin fibers, preferably human keratin fibers, more preferably human hair, characterized in that it comprises the steps of:

a) providing the ready-to-use composition as defined above, b) applying the composition onto keratin fibers, c) leaving the composition onto keratin fibers for a time period of 1 min to 45 min, d) rinsing-off the composition and/or shampooing the keratin fibers when the desired amount of lightening is achieved, e) optionally drying the hair.

It is preferred that between process step c) and d) the end point of the bleaching process is judged by the naked human eye while comparing the treated keratin fibers with a keratin fiber standard which possesses the desired degree of lightening. Keratin, human hair, fiber standards are available for each brand in the form of colour charts which are suitable for use in the process of the present invention.

Another object of the present invention is a kit-of-parts for bleaching keratin fibers, preferably human keratin fibers, more preferably human hair, characterized in that a first separately packed container comprises an aqueous or anhydrous first composition as defined above, a second separately packed container comprises an aqueous second composition as defined above, and a third separately packed container comprises a third composition as defined above.

Pigments and Third Composition

The third composition of the present invention preferably is an aqueous composition and preferably has a pH in the range of 4 to 7. The third composition comprises the pigments according to the present invention.

The term pigment according to the present invention is to be understood as particulate matter which does not dissolve in water at 25° C. under atmospheric conditions. Preferably the pigments have an average particle size by volume in the range of 250 nm to 100 µm, more preferably in the range of 500 nm to 75 µm. A suitable instrument for particle size measurement by volume is the Malvern Mastersizer static light scattering instrument equipped with a powder measurement cell. The skilled person notes that for non-spherical particles an equivalent diameter is retrieved by this measurement method and that the preferred size ranges for this invention apply to the equivalent diameters for non-spherical pigments.

Pigments suitable for the present invention may have any possible shapes. The color of pigments is assessed by a judgement with the naked human eye of a dispersion of pigments in water at 0.1% by weight pigment concentration at 25° C. and atmospheric conditions through a path length of 1 cm upon 10 s of shaking the dispersion by hand and allowing for a settlement time of less than 5 s.

Suitable brown pigments for the purpose of the invention are, for example, natural or synthetic brown iron oxides.

Suitable blue pigments are, for example, ultramarine blue, ferric blue, Prussian blue, Persian blue, cobalt blue, han blue, azurite, and manganese blue.

Suitable green pigments are, for example, chrome green, viridian, cobalt green, malachite, cupric acetate, and green earth.

In one aspect of the present invention, black pigment(s) is/are selected from carbon black, graphite, fullerene, carbon nanotubes and/or megatubes, charcoal, soot, titanium black, CI 77268, and/or pigments based on black iron oxide, brown pigment(s) is/are selected from brown iron oxides, blue pigment(s) is/are selected from ultramarine blue, ferric blue, Prussian blue, Persian blue, cobalt blue, han blue, no azurite, and manganese blue, green pigment(s) is/are selected from chrome green, viridian, cobalt green, malachite, cupric acetate, and green earth, and/or mixtures thereof.

Suitable black pigments based on black iron oxide are for example disclosed in EP2686386, but the selection of black pigments based on black iron oxide is not limited to this disclosure.

The preferred black pigment is selected from graphite and/or carbon black, and/or mixtures thereof, wherein the most preferred black pigment is carbon black.

The total concentration of pigments in the third composition is in the range of 1% to 30% by weight, preferably in the range of 2% to 20% by weight, more preferably in the range of 3% to 15% by weight, calculated to the total of the third composition.

First Composition

The first composition is either anhydrous or aqueous.

Anhydrous First Composition

The anhydrous first composition further comprises one or more bleaching compound(s) selected from persalt(s) and/or peroxy salt(s).

Suitable persalts and/or peroxy salts are sodium persulfate, potassium persulfate and ammonium persulfate, earth alkali peroxides such as magnesium peroxide, melamine peroxide or urea peroxide or phtholimidoperoxy hexanoic acid. The preferred persalts are sodium persulfate and/or potassium persulfate and/or ammonium persulfate. The total concentration of persalts and/or peroxysalts in the anhydrous first composition is in the range of 1% to 80% by weight, preferably 2% to 60% by weight, more preferably 5% to 50% by weight, and most preferably 10% to 45% by weight, calculated to total of the anhydrous first composition.

Aqueous First Composition

Preferably, the aqueous first composition is free of persalt(s) and/or peroxy salt(s).

Furthermore, it is preferable that the aqueous first composition comprises oxidative dye precursors at a concentration of less or equal to 0.5% by weight, preferably less or equal to 0.25% by weight, calculated to the total of the aqueous first composition.

The aqueous or anhydrous first composition and/or the third composition further comprise an alkalizing agent with a pK$_b$ of less than 12, measured at 25° C. under atmospheric conditions by acid-base titration.

Preferably, the alkalizing agent is selected from sodium metasilicate and/or ammonia and/or its salts and/or alkali or earth alkali carbonates and/or bicarbonates and/or an organic alkyl and/or alkanol amine and/or their salts according to the general structure

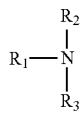

wherein $R_1$, $R_2$, and $R_3$ are independently selected from H, linear $C_1$-$C_6$ alkyl which may be substituted with one hydroxyl group, or branched $C_3$-$C_{12}$ alkyl or alkanol, wherein at least one of $R_1$, $R_2$, or $R_3$ is different from H.

Compounds corresponding to the structure of above are, for example, mono-/di-/tri-ethanolamine, mono-/di-/trimethylamine, and mono-/di-/triethylamine.

Further suitable alkalizing agents are alkali or earth alkali carbonates and/or bicarbonates. Non-limiting examples are sodium and potassium carbonate, magnesium carbonate and sodium bicarbonate.

Equally suitable alkalizing agents are guanidine and/or urea.

Preferably the compositions comprise one or more alkalizing agent(s) is selected from monoethanolamine and/or diethanolamine and/or 2-aminomethyl propanol and/or sodium metasilicate, and/or ammonia and/or its salt(s) and/or their mixtures.

The total concentration of one or more alkalizing agent(s) in the aqueous or anhydrous first composition and/or in the third composition is/are in the range from 1% to 20% by weight, preferably 2% to 15% by weight, calculated to the total of each composition.

The aqueous or anhydrous first composition and/or aqueous second composition and/or third composition further comprise one or more ammonium salt(s) different from persalt(s) and peroxy salt(s).

Suitable ammonium salts different from peroxy salt(s) and persalt(s) are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. The compositions may also comprise mixtures of ammonium salts.

Preferred thereof are the ammonium phosphates, such as ammonium dihydrogen phosphate, diammonium hydrogen phosphate, diammonium sodium phosphate, ammonium sodium hydrogen phosphate or ammonium disodium phosphate, ammonium chloride, ammonium sulfate and diammonium hydrogen citrate.

The total concentration of one or more ammonium salt(s) different from peroxy salt(s) and persalt(s) in the ready-to-use mixture is in the range from 0.1% to 20% by weight, calculated to the total of the ready-to-use mixture.

Aqueous Second Composition

The aqueous second composition comprises hydrogen peroxide at a concentration in the range of 0.5% to 20% by weight, preferably in the range of 1% to 15% by weight, more preferably in the range of 1.5% to 12% by weight, calculated to the total of the aqueous second composition.

Surfactants

Any of the aqueous or anhydrous first and/or aqueous second and/or third composition(s) may comprise(s) surfactants selected from anionic, non-ionic, cationic, zwitterionic and/or amphoteric surfactants, and/or their mixtures.

Suitable anionic surfactants are alkyl sulfate or preferably ethoxylated alkyl ether sulfate surfactant or mixtures thereof with an alkyl chain length of $C_{10}$ to $C_{22}$.

Suitable surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myristyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

Suitable non-ionic surfactants are in general all commonly known non-ionic surfactants available on the market.

Suitable nonionic surfactants are alkyl polyglycosides according to the general structure:

$$R^{23}O(R^{24}O)_t Z_x$$

Wherein Z denotes a reducing carbohydrate with $C_5$ to $C_6$, $R^{23}$ is an alkyl group with $C_8$ to $C_{18}$, $R^{24}$ is ethyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The preferred compound according to the structure of above is decyl glucoside.

Suitable examples for non-ionic surfactants are fatty alcohol ethoxylates of the following general structure $$R^{18}(OCH_2CH_2)_{n4}OH$$

wherein $R^{18}$ is straight or branched, saturated or unsaturated alkyl chain which may be synthetic or natural with a C chain length in the range of 8 to 40, preferably 9 to 30 and more preferably 9 to 24 and n4 is a number in the range of 5 to 40, preferably 9 to 30.

Further suitable nonionic surfactants are polypropylene glycol ethers of fatty alcohol according to general structure $$R^{19}(OCH_2(CH_3)CH_2)_{n5}OH$$

wherein $R^{19}$ is straight or branched, saturated or unsaturated fatty alcohol which may be synthetic or natural with a C chain length in the range of 8 to 40, preferably 9 to 30 and more preferably 9 to 24 and n5 is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Stearyl ether and PPG-15 Stearyl ether.

Further suitable nonionic surfactants are polyethylene glycol fatty acid esters of the following general structure $$R^{20}C(O)(OCH_2CH_2)_{n6}OH$$

wherein $R^{20}$ is straight or branched, saturated or unsaturated alkyl group which may be synthetic or natural with a C chain length in the range of 7 to 39, preferably 9 to 29 and more preferably 9 to 23 and n6 is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8 Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are polypropylene glycol fatty acid esters of the following general structure $$R^{21}C(O)(OCH_2(CH_3)CH_2)_{n8}OH$$

wherein $R^{21}$ is straight or branched, saturated or unsaturated alkyl group which may be synthetic or natural with a C chain length in the range of 7 to 39, preferably 9 to 29 and more preferably 9 to 23 and n8 is a number in the range of 1 to 40, preferably 9 to 30.

Suitable non-limiting examples are PPG-15 Isostearate, PPG-9 Laurate, PPG-26 Oleate and PPG-36 Oleate.

Further suitable nonionic surfactants are polyethylene glycol and polypropylene glycol ether of fatty alcohols of the following general structure $$R^{22}(OCH_2(OH_3)CH_2)_{n9}(OCH_2CH_2)_{n10}OH$$

wherein $R^{22}$ is straight or branched, saturated or unsaturated alkyl group which may be synthetic or natural with a C chain length in the range of 7 to 39, preferably 9 to 29 and more preferably 9 to 23 and n9 and n10 may be the same or different and are a number in the range of 1 to 40.

Further suitable nonionic surfactants are ethoxylated triglycerides. Well known and commonly used examples are ethoxylated castor oil such as PEG-40 hydrogenated castor oil or and PEG-60 hydrogenated castor oil.

Suitable cationic surfactants are according to the general structure

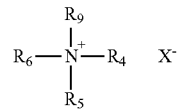

where $R^5$ is a saturated or unsaturated, branched or linear alkyl chain with 8-22 C atoms or $$R^7CONH(CH_2)_n$$

where $R^7$ is saturated or unsaturated, branched or linear alkyl chain with 7-21 C atoms and n has typical value of 1-4 or $$R^8COO(CH_2)_n$$

where $R^8$ is saturated or unsaturated, branched or linear alkyl chain with 7-21 C atoms and n has typical value of 1-4, and $R^4$ is H or unsaturated or saturated, branched or linear alkyl chain with 1-22 C atoms or

or

where $R^7$, $R^8$ and n are same as above.

$R^9$ and $R^6$ are H or lower alkyl chain with $C_1$-$C_4$, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Suitable amphoteric and/or zwitterionic surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

The total concentration of surfactants in each composition part of the present invention is in the range of 0.5% to 15% by weight, preferably 1% to 12% by weight, more preferably 1.5% to 10% by weight, calculated to the total each composition.

Cosmetic Form, Thickening Agents, Additional Compounds

The three-part composition according to the present invention may be in any suitable form for cosmetic application. It is preferred that the aqueous first and/or aqueous second and/or third composition is/are an aqueous suspension and/or emulsion. The anhydrous first composition may be in the form of a powder, a dust-free powder, or a non-aqueous liquid dispersion. Furthermore, the aqueous or anhydrous first and/or aqueous second and/or third compositions may comprise a thickening agent, preferably a polymeric thickening agent, more preferably a polymeric thickening agent selected from associative and/or non-associative polymers.

Preferably, the third composition comprises a thickening agent, preferably a polymeric thickening agent, more preferably a polymeric thickening agent selected from associative and/or non-associative polymers.

In a preferred aspect of the present invention, the thickening agents are thickening polymers selected from anionic, nonionic, cationic and amphoteric polymers, preferably selected from polymers resulting in a solution and/or dispersion with a viscosity of at least 500 mPa·s measured at a polymer concentration of 1% by weight in water and at 20° C. with a Brookfield viscometer, such as at 10 rpm for 1 min, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, guar gum, and polymeric anionic thickeners, namely Carbomer and its derivatives.

Of particular advantageous use are thickeners which are commonly known as associative thickeners. Preferred are copolymers and/or crosspolymers which comprise an acrylate and/or methacrylate monomer unit and at least one more hydrophobic unit such as alkyl chains. Examples are acrylates/c10-30 alkyl acrylate crosspolymer, acrylates/steareth-20 methacrylate copolymer, acrylates/stearyl acrylate/dimethicone methacrylate copolymer, acrylates/beheneth-25 methacrylate copolymer, acrylates/lauryl acrylate/stearyl acrylate/ethylamine oxide methacrylate copolymer.

In a preferred aspect of the present invention the aqueous first and/or third composition is/are an aqueous suspension and/or emulsion and comprise(s) a thickening agent, preferably a polymeric thickening agent, more preferably a polymeric thickening agent selected from associative and/or non-associative polymers.

The aqueous or anhydrous first and/or aqueous second and/or third composition may comprise thickening agents at a total concentration in the range of 0.1% to 5%, preferably, 0.2% to 3%, more preferably 0.25% to 2.5% and most preferably 0.3% to 2% by weight calculated to the total of the each composition.

In case where the aqueous first and/or aqueous second and/or third composition is/are an emulsion or a dust-free anhydrous powder, the compositions comprise lipophilic compounds selected from natural and/or vegetable oils, petrolatum-based compounds, linear or branched, saturated or unsaturated fatty alcohols with $C_{12}$ to $C_{22}$, and fatty acid esters consisting of linear or branched, saturated or unsaturated fatty acids with $C_{12}$ to $C_{22}$ being esterified with linear or branched primary alcohols with $C_3$ to $C_{12}$, and silicones.

Suitable natural and/or vegetable oils are olive oil, almond oil, avocado oil, wheatgerm oil, and castor oil.

Suitable petrolatum-based compounds are liquid paraffins, especially paraffinum perliquidum and paraffinum subliquidum, and mineral oil, in particular white mineral oil.

Suitable comprises fatty compounds selected from linear or branched, saturated or unsaturated fatty alcohols with $C_{12}$ to $C_{22}$ are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures, such as cetearyl alcohol.

Suitable examples for fatty acid esters consisting of linear or branched, saturated or unsaturated fatty acids with $C_{12}$ to $C_{22}$ being esterified with linear or branched primary alcohols with $C_3$ to $C_{18}$ are octyl palmitate, isocetyl palmitate, isopropyl palmitate, octyl stearate, oleyl oleate, and myristyl myristate, as well as their mixtures.

Suitably, the compositions may also comprise lipophilic ingredients such as silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; $C_{10}$- to $C_{36}$-fatty acid triglycerides, as well as their mixtures.

The total concentration of lipophilic compounds in the aqueous or anhydrous first and/or aqueous second and/or third composition is in the range of 0.5% to 20% by weight, preferably from 1% to 15% by weight, and more preferably from 3% to 10% by weight, calculated to the total of each composition.

The aqueous or anhydrous first and/or aqueous second and/or third composition may further comprise an organic solvent. In principle, all water-miscible organic solvents are suitable for the purpose of the invention. Suitable non-limiting examples are C2-C4 monoalcohols and/or C2-3 dialcohols and/or and glycerol. Preferred C2-C4 monoalcohols and/or C2-3 dialcohols solvents are ethanol, n-propanol, isopropanol, butanol, ethylene glycol, propylene glycol. Further suitable aromatic alcohols are phenoxyethanol and benzyl alcohol.

The total concentration of organic solvents is in the range of 0.5% to 10% by weight, preferably 1% to 8% by weight, more preferably 1.5% to 5% by weight, calculated to the total of each of the compositions.

In an aspect of the present invention the third composition is a liquid non-aqueous composition. A suitable dispersion medium is a liquid polyol, especially liquid polyethylene glycol such as PEG-400 for the pigments and/or alkalizing agents and/or thickening polymers. In this case the concentration of organic solvents may be higher as disclosed above to disperse the pigments.

Ready-to-Use Mixture

For preparation of the ready-to-use mixture, the composition of the present invention has a mixing ratio of the first:second:third composition in the range of 1:1:0.1 to 1:2:0.5 by weight.

Preferably the pH of the ready-to-use mixture as defined above is in the range of 8 to 11, more preferably in the range of 8.5 to 10.

Bleaching Endpoint Judgement

The keratin fibers are immersed with the ready-to-use composition comprising the three-part bleaching composition according to the present invention and then the keratin fibers are allowed to process. The bleaching reaction is stopped by judgement of the naked human eye when the desired degree of lightening is achieved. To visually reach the target degree of lightening, a set of comparative hair strands is supplied to the hair dresser including hair streaks with the desired degree of lightening to allow experts for a visual comparison. Upon decision by the expert to stop the reaction by visual comparison with the help of the supplied target hair streaks, the keratin fibers are washed for 60 s with a commercial shampoo. The keratin fibers may then be dried e.g. by blow drying.

The following examples are to illustrate the present invention, but not to limit it.

EXAMPLES

Example 1

The following aqueous first composition was prepared by conventional mixing techniques:

|  | % by weight |
| --- | --- |
| Ammonium hydroxide (28% active) | 10.0 |
| Sodium laureth sulfate | 2.0 |
| Dehydroxanthan gum | 0.5 |
| Water | ad 100.0 |

The following second aqueous composition was prepared:

|  | % by weight |
| --- | --- |
| Hydrogen peroxide (30% active) | 30.0 |
| Phosphoric acid | ad pH 3.5 |
| Water | ad 100.0 |

The following aqueous third compositions were prepared:

|  | % by weight |
| --- | --- |
| Carbon black | 1.1 |
| Cetearyl alcohol | 5.0 |
| Sodium laureth sulfate | 3.0 |
| Water | ad 100.0 |

The first:second:third compositions were mixed in a ratio of 1:2:0.1 by weight prior to application onto hair. The resulting pH was measured at 10.0.

Example 2

The following aqueous first composition was prepared:

|  | % by weight |
| --- | --- |
| Ammonium hydroxide (28% active) | 5.0 |
| 2-aminomethyl propanol | 1.0 |
| Sodium bicarbonate | 1.5 |
| Cetearyl alcohol | 10.0 |
| Sodium laureth sulfate | 3.0 |
| Ceteareth-20 | 1.5 |
| p-phenylene diamine | 0.1 |
| Resorcinol | 0.08 |
| Acrylates copolymer | 0.1 |
| Water | ad 100.0 |

The following aqueous second composition was prepared:

|  | % by weight |
| --- | --- |
| Stearyl alcohol | 10.0 |
| PEG-40 hydorgenated castor oil | 2.0 |
| Sodium lauryl sulfate | 1.0 |
| Hydrogen peroxide | 9.0 |
| Phosphoric acid | ad pH 3.0 |
| Water | ad 100.0 |

The following aqueous third composition was prepared:

|  | % by weight |
| --- | --- |
| Cetearyl alcohol | 10.0 |
| Sodium laureth sulfate | 3.0 |
| PEG-40 hydrogenated castor oil | 1.0 |
| Graphite | 15.0 |
| Carbon black | 5.0 |
| 2-aminomethyl propanol | 2.0 |
| Acrylates copolymer | 0.5 |
| Water | ad 100.0 |

The pH of the third composition was 9.2.

The compositions were mixed in a weight ratio of first:second:third composition of 1:1:0.5 and a satisfactory black colored ready-to-use mixture was received. The resulting pH was measured at 9.9.

In the aqueous third composition carbon black was exchanged in favour of titanium black, CI77268, fullerene, charcoal, carbon nanotubes at the same concentration. A satisfactory black colored ready-to-use mixture was obtained.

Example 3

The following anhydrous first composition was prepared by conventional mixing techniques:

|  | % by weight |
| --- | --- |
| Ammonium persulfate | 35.0 |
| Potassium persulfate | 25.0 |
| Sodium laureth sulfate | 6.0 |
| Sodium metasilicate | 5.0 |
| 2-aminomethyl propanol | 2.0 |
| White mineral oil | 3.0 |
| Dehydroxanthan gum | 1.0 |
| Diatomaceous earth | ad 100.0 |

The following second aqueous composition was prepared:

|  | % by weight |
| --- | --- |
| Hydrogen peroxide (30% active) | 30.0 |
| Phosphoric acid | ad pH 3.5 |
| Water | ad 100.0 |

The following aqueous third compositions were prepared:

| Ingredients | Inventive [% by weight] | Comparative [% by weight] |
| --- | --- | --- |
| Carbon black | 1.1 | — |
| Cetearyl alcohol | 5.0 | 5.0 |
| Sodium laureth sulfate | 3.0 | 3.0 |
| Water | Ad 100.0 | |

The first:second:third compositions were mixed in a ratio of 1:2:0.1 by weight prior to application onto hair. The resulting pH was measured at 9.5.

Caucasian dark hair streaks (21 cm long, 2 g per streak) were purchased from Fischbach+Miller Haar, Laupheim, Germany. The streaks were immersed with 2 g of either the inventive or comparative composition and allowed to process. The bleaching reaction was stopped by judgement of the naked human eye when the desired degree of lightening was achieved. The experiments were repeated 5 times per treatment group wherein each streak was judged by a different laboratory expert on the time point of when to stop the bleaching reaction. To visually reach the target degree of lightening, a set of comparative hair strands was supplied to the experts including hair streaks with the desired degree of lightening to allow experts for a visual comparison. Measurements confirmed that the lightening difference between the starting point and the target hair streak corresponded to $\Delta L=50$. Upon decision by each expert to stop the reaction by visual comparison with the help of the supplied target hair streaks, each test hair streak was immediately washed for 60 s with a commercial shampoo available under the brand name Goldwell Dualsenses Deep Cleansing Shampoo. The hair streaks were then blow dried. For final evaluation, $\Delta L$ values were calculated based on the lightening value L measurement with a Datacolor 45G CT instrument purchased from Datacolor Inc., Lawrenceville, N.J., USA. The starting L value was taken from the untreated hair streaks.

The following results were obtained:

| Experts | Inventive composition [$\Delta L$ value] | Comparative composition [$\Delta L$ value] |
| --- | --- | --- |
| Expert 1 | 37.60 | 26.44 |
| Expert 2 | 41.09 | 28.04 |
| Expert 3 | 41.97 | 27.66 |
| Expert 4 | 43.50 | 28.66 |
| Expert 5 | 42.31 | 28.20 |
| Average | 41.29 | 27.80 |
| SD | 2.24 | 0.84 |
| Average distance to target level of 50 | 8.71 | 22.20 |

The bleaching processes were stopped by the experts according to their visual judgement. For the comparative composition, the reaction was stopped at around 20 min of process time, and for the inventive composition around 25 min upon application of the ready-to-use bleaching composition. As a result, it was unexpectedly found that the inventive composition comprising pigment allowed the experts to receive a higher degree of lightening which is by far closer to the desired degree of $\Delta L=50$. Consequently the experts were less prone to stop the bleaching reaction too early and to discover an undesired low lightening degree after shampooing.

Example 4

The following anhydrous first composition was prepared:

|  | % by weight |
| --- | --- |
| Ammonium persulfate | 25.0 |
| Sodium persulfate | 35.0 |
| Ceteareth-30 | 7.5 |
| Monoethanolamine | 6.0 |
| Sodium metasilicate | 2.0 |
| 2-amino-methyl propanol | 1.0 |
| Liquid paraffin | 3.0 |
| Diatomaceous earth | ad 100.0 |

The following aqueous second composition was prepared:

|  | % by weight |
| --- | --- |
| Stearyl alcohol | 10.0 |
| PEG-40 hydorgenated castor oil | 2.0 |
| Sodium lauryl sulfate | 1.0 |
| Hydrogen peroxide | 9.0 |
| Phosphoric acid | ad pH 3.0 |
| Water | ad 100.0 |

The following aqueous third composition was prepared:

|  | % by weight |
| --- | --- |
| Cetearyl alcohol | 10.0 |
| Sodium laureth sulfate | 3.0 |
| PEG-40 hydrogenated castor oil | 1.0 |
| Graphite | 15.0 |
| Carbon black | 5.0 |
| 2-aminomethyl propanol | 2.0 |
| Acrylates copolymer | 0.5 |
| Water | ad 100.0 |

The pH of the third composition was 9.2.

The compositions were mixed in a weight ratio of first:second:third composition of 1:1:0.5 and a satisfactory black colored ready-to-use mixture was received. The resulting pH was measured at 9.9.

In the aqueous third composition carbon black was exchanged in favour of titanium black, CI77268, fullerene, charcoal, carbon nanotubes at the same concentration. A satisfactory black colored ready-to-use mixture was obtained.

The following examples are within the scope of the present invention.

Example 5

| Anhydrous first composition | |
|---|---|
| | % by weight |
| Ammonium persulfate | 35.0 |
| Sodium persulfate | 35.0 |
| PEG-40 hydrogenated castor oil | 6.0 |
| Monoethanolamine | 3.0 |
| Sodium metasilicate | 2.0 |
| 2-amino-methyl propanol | 1.0 |
| Diatomaceous earth | ad 100.0 |

| Aqueous second composition | |
|---|---|
| | % by weight |
| Hydrogen peroxide (30% active) | 30.0 |
| Phosphoric acid | ad pH 3.5 |
| Acrylates/steareth-20 methacrylate copolymer | 1.0 |
| Water | ad 100.0 |

| Aqueous third composition | |
|---|---|
| | % by weight |
| Carbon black | 30.0 |
| Xanthan gum | 5.0 |
| Water | ad 100.0 |

The first:second:third composition were mixed in a weight ratio of 1:2:0.1. The pH of the ready-to-use mixture was measured at 9.3. The aqueous third composition had a pH of 6.5.

Example 6

| Aqueous third composition | |
|---|---|
| | % by weight |
| Carbon black | 1.5 |
| Graphite | 1.0 |
| Charcoal | 1.0 |
| Cetearyl alcohol | 2.0 |
| Olive oil | 0.5 |
| Ceteareth-30 | 1.0 |
| Dehydroxanthan gum | 1.0 |
| Water | ad 100.0 |

The aqueous third composition was mixed with the anhydrous first composition and aqueous second composition of example 5 or. The mixing weight ratio of example 5 or 8 was kept as well.

Either single one of the black pigments from above was replaced by titanium black, CI77268, and carbon nanotubes at any of the concentrations of the examples. A satisfactory black composition was received.

White mineral oil in the aqueous third composition was replaced with either olive oil, polydimethylsiloxane with a viscosity of 10,000 mPas, and isopropyl myristate. A satisfactory black composition was received.

Example 7

| Aqueous third composition | |
|---|---|
| | % by weight |
| Ultramarine blue | 10.0 |
| Stearyl alcohol | 8.0 |
| Ceteareth-30 | 1.0 |
| Sodium laureth sulfate | 3.0 |
| Cetrimonium chloride | 0.5 |
| Ammonium chloride | 0.8 |
| Dehydroxanthan gum | 1.0 |
| Water | ad 100.0 |

The aqueous third composition was mixed with the anhydrous first and aqueous second composition of example 5 or 8 in the same weight ratio. A satisfactory blue ready-to-use mixture was received.

Ultramarine blue was replaced with brown iron oxides or chrome green. A satisfactory brown or green colored ready-to-use composition was received, respectively.

Example 8

| Aqueous first composition | |
|---|---|
| | % by weight |
| Ammonium hydroxide (28% active) | 5.0 |
| Monoethanolamine | 3.5 |
| Stearyl alcohol | 5.0 |
| Sodium laureth sulfate | 1.0 |
| Ceteareth-20 | 1.5 |
| 1,3-diamino benzene | 0.05 |
| 4-amino phenol | 0.05 |
| Water | ad 100.0 |

| Aqueous second composition | |
|---|---|
| | % by weight |
| Hydrogen peroxide (30% active) | 30.0 |
| Phosphoric acid | ad pH 3.5 |
| Acrylates/steareth-20 methacrylate copolymer | 1.0 |
| Water | ad 100.0 |

| Aqueous third composition | |
|---|---|
| | % by weight |
| Carbon black | 30.0 |
| Xanthan gum | 5.0 |
| Water | ad 100.0 |

The first:second:third composition were mixed in a weight ratio of 1:2:0.1. The pH of the ready-to-use mixture was measured at 9.3. The aqueous third composition had a pH of 6.5.

Example 9

| Third composition | |
|---|---|
| | % by weight |
| Carbon black | 30.0 |
| Xanthan gum | 5.0 |
| PEG-400 | ad 100.0 |

The first:second:third compositions were mixed in a weight ratio of 1:2:0.1. The pH of the ready-to-use mixture was measured at 9.3.

The invention claimed is:

1. A kit for a bleaching composition for keratin fibers, comprising separately:
    a) an anhydrous first composition comprising one or more alkalizing agents, and one or more bleaching compounds;
    b) an aqueous second composition comprising hydrogen peroxide; and
    c) a third composition, comprising one or more pigments selected from black pigment, brown pigment, blue pigment and green pigment,
    wherein, when the components of the kit are mixed to form the bleaching composition, the bleaching composition has a pH in the range of 8 to 12, and
    the total concentration of pigments in the third composition is more than 0.6% by weight, calculated to the total of the third composition.

2. The kit according to claim 1 wherein:
    the black pigment is at least one selected from carbon black, graphite, fullerene, carbon nanotubes, carbon megatubes, charcoal, soot, titanium black, CI 77268, and a pigment based on black iron oxide;
    the brown pigment is selected from brown iron oxides;
    the blue pigment is selected from ultramarine blue, ferric blue, Prussian blue, Persian blue, cobalt blue, han blue, azurite, and manganese blue; and
    the green pigment is at least one selected from chrome green, viridian, cobalt green, malachite, cupric acetate, and green earth, and mixtures thereof.

3. The kit according to claim 2, wherein the black pigment is at least one selected from graphite, carbon black, and mixtures thereof.

4. The kit according to claim 1, wherein the total concentration of pigments in the third composition is more than 1% by weight, calculated to the total of the third composition.

5. The kit according to claim 1, wherein the anhydrous first composition comprises one or more bleaching compound selected from a persalt and a peroxy salt.

6. The kit according to claim 1, wherein at least one of the first composition and the third composition comprises at least one alkalizing agent selected from monoethanolamine, diethanolamine, 2-aminomethyl propanol, sodium metasilicate, ammonia, ammonia salts, and mixtures thereof.

7. The kit according claim 1, wherein one or more of the anhydrous first composition, the aqueous second composition and the third composition comprise one or more ammonium salts different from persalt and peroxy salt.

8. The kit according to claim 1, wherein the third composition is at least one of an aqueous suspension and an emulsion and comprises a thickening agent.

9. The kit according to claim 1, wherein at least one of the first composition, second composition, and third composition comprises one or more surfactants selected from anionic surfacants, non-ionic surfactants, cationic surfactants, zwitterionic surfactants, amphoteric surfactants, and mixture thereof.

10. The kit according to claim 9, wherein the total concentration of surfactants in each composition part is in the range of 0.5% to 15% by weight, calculated to the total of such composition.

11. The kit according to claim 1, wherein that the mixing ratio of the first:second:third composition is in the range of 1:1:0.1 to 1:2:0.5 by weight.

12. The kit according to claim 1, wherein the third composition is an aqueous composition and has a pH in the range of 4 to 7.

13. A method for bleaching keratin fibers, comprising the steps of:
    a) providing the kit of claim 1 and mixing the first, second and third components together to produce a mixed bleaching composition;
    b) applying the mixed bleaching composition onto keratin fibers;
    c) leaving the mixed bleaching composition on the keratin fibers for a time period of 1 min to 45 min;
    d) at least one of rinsing-off the bleaching composition from the keratin fibers and shampooing the keratin fibers when the desired amount of lightening is achieved; and
    e) optionally drying the keratin fibers.

14. The method according to claim 13, wherein, between process step c) and step d), an end point of the bleaching process is judged by a naked human eye while comparing the treated keratin fibers with a keratin fiber standard which possesses the desired degree of lightening.

15. A bleaching composition for bleaching keratin fibers, comprising
    a) an anhydrous first composition comprising one or more alkalizing agents, and one or more bleaching compounds,
    b) an aqueous second composition comprising hydrogen peroxide, and
    c) a third composition, comprising one or more pigments selected from black pigment, brown pigment, blue pigment and green pigment,
    wherein
    the bleaching composition has a pH in the range of 8 to 12, and
    the total concentration of one or more pigments in the third composition is more than 0.6% by weight, calculated to the total of the third composition.

* * * * *